US009504412B2

(12) United States Patent
Schaible

(10) Patent No.: US 9,504,412 B2
(45) Date of Patent: Nov. 29, 2016

(54) METHOD AND SYSTEM TO DERIVE GLYCEMIC PATTERNS FROM CLUSTERING OF GLUCOSE DATA

(71) Applicant: Thomas Schaible, Phoenixville, PA (US)

(72) Inventor: Thomas Schaible, Phoenixville, PA (US)

(73) Assignee: LifeScan, Inc., Wayne, PA (US)

( * ) Notice: Subject to any disclaimer, the term of this patent is extended or adjusted under 35 U.S.C. 154(b) by 1018 days.

(21) Appl. No.: 13/621,499

(22) Filed: Sep. 17, 2012

(65) Prior Publication Data

US 2014/0081103 A1  Mar. 20, 2014

(51) Int. Cl.
| | |
|---|---|
| A61B 5/1486 | (2006.01) |
| A61B 5/155 | (2006.01) |
| A61B 5/157 | (2006.01) |
| A61B 5/145 | (2006.01) |
| A61B 5/15 | (2006.01) |
| A61B 5/00 | (2006.01) |

(52) U.S. Cl.
CPC ......... *A61B 5/1486* (2013.01); *A61B 5/14532* (2013.01); *A61B 5/14865* (2013.01); *A61B 5/155* (2013.01); *A61B 5/157* (2013.01); *A61B 5/150022* (2013.01); *A61B 5/15087* (2013.01); *A61B 5/150854* (2013.01); *A61B 5/150862* (2013.01); *A61B 5/4839* (2013.01); *A61B 5/0022* (2013.01); *A61B 5/0031* (2013.01); *A61B 5/150358* (2013.01)

(58) Field of Classification Search
CPC .............. A61B 5/0022; A61B 5/0031; A61B 5/14532; A61B 5/1486; A61B 5/14865; A61B 5/155; A61B 5/157; A61B 5/4839
See application file for complete search history.

(56) References Cited

U.S. PATENT DOCUMENTS

| | | | | |
|---|---|---|---|---|
| 5,251,126 A * | 10/1993 | Kahn | ............... | G01N 35/00871 128/923 |
| 5,307,263 A * | 4/1994 | Brown | ................. | A61B 5/0022 128/904 |
| 5,822,715 A | 10/1998 | Worthington et al. | | |
| 6,390,986 B1 | 5/2002 | Curcie et al. | | |
| 8,317,699 B2 * | 11/2012 | Weinert | ................ | G06F 19/322 600/365 |
| 8,758,245 B2 * | 6/2014 | Ray | ........................ | G06F 19/345 600/347 |
| 8,834,367 B2 * | 9/2014 | Laan | ..................... | G06F 19/322 600/365 |
| 2003/0208113 A1 * | 11/2003 | Mault | ................ | A61B 5/14532 600/316 |
| 2005/0159656 A1 | 7/2005 | Hockersmith et al. | | |
| 2006/0020192 A1 * | 1/2006 | Brister | ................. | A61B 5/0002 600/345 |
| 2006/0264895 A1 | 11/2006 | Flanders | | |
| 2007/0016449 A1 * | 1/2007 | Cohen | ................. | G06F 19/3406 705/3 |
| 2007/0179352 A1 * | 8/2007 | Randlov | ............. | G06F 19/3487 600/300 |
| 2008/0071580 A1 | 3/2008 | Marcus et al. | | |
| 2008/0234943 A1 | 9/2008 | Ray et al. | | |
| 2008/0234992 A1 | 9/2008 | Ray et al. | | |
| 2008/0235053 A1 | 9/2008 | Ray et al. | | |
| 2009/0018779 A1 * | 1/2009 | Cohen | ................. | G06F 19/3406 702/19 |

(Continued)

FOREIGN PATENT DOCUMENTS

| | | |
|---|---|---|
| EP | 1418523 A | 5/2004 |
| WO | WO 00/04512 A2 | 1/2000 |

(Continued)

*Primary Examiner* — Navin Natnithithadha

(57) ABSTRACT

Described are methods and systems for determining clusters of glucose data that can be utilized to provide insights to the person with diabetes, such as, for example, when a certain number of measurements during a predetermined time period is less than a predetermined threshold so that the subject is notified that the number of glucose measurements is less than optimum for management of diabetes.

11 Claims, 7 Drawing Sheets

(56) References Cited

U.S. PATENT DOCUMENTS

| | | | |
|---|---|---|---|
| 2009/0030733 A1* | 1/2009 | Cohen | G06F 19/3406 705/3 |
| 2009/0150186 A1* | 6/2009 | Cohen | G06F 19/3406 705/3 |
| 2012/0059673 A1* | 3/2012 | Cohen | G06F 19/3406 705/3 |
| 2012/0232520 A1* | 9/2012 | Sloan | A61B 5/14532 604/504 |
| 2014/0083867 A1* | 3/2014 | Schaible | A61B 5/14532 205/782 |

FOREIGN PATENT DOCUMENTS

| | | |
|---|---|---|
| WO | WO 01/00086 A1 | 1/2001 |
| WO | WO 2005/093629 A2 | 10/2005 |
| WO | WO 2007/005170 A2 | 1/2007 |
| WO | WO 2008/071218 A1 | 6/2008 |

* cited by examiner

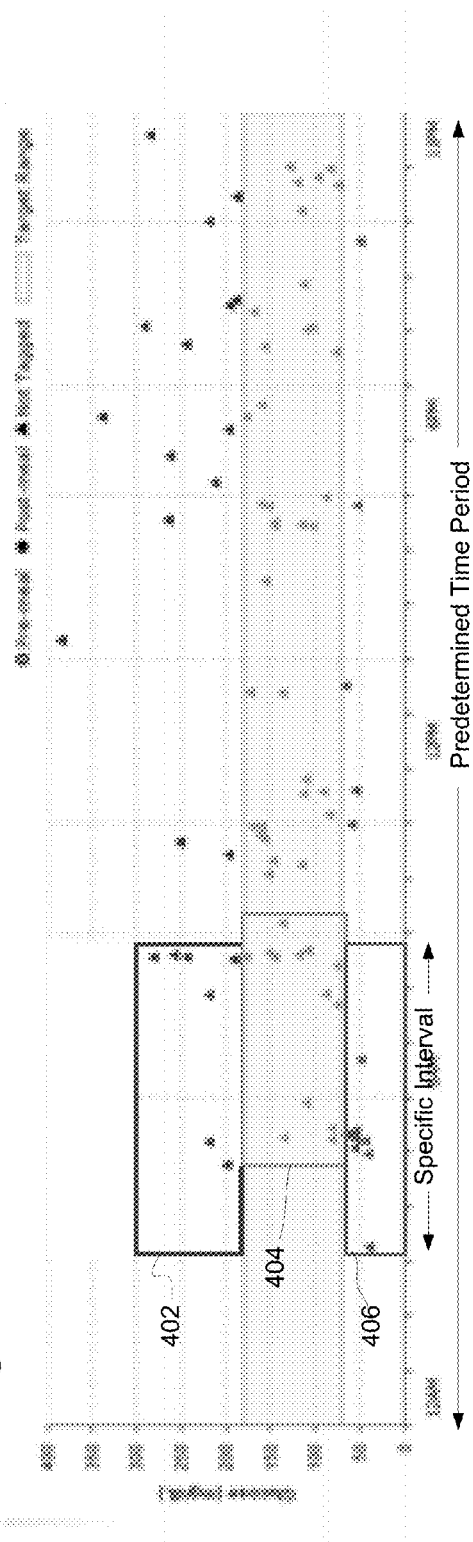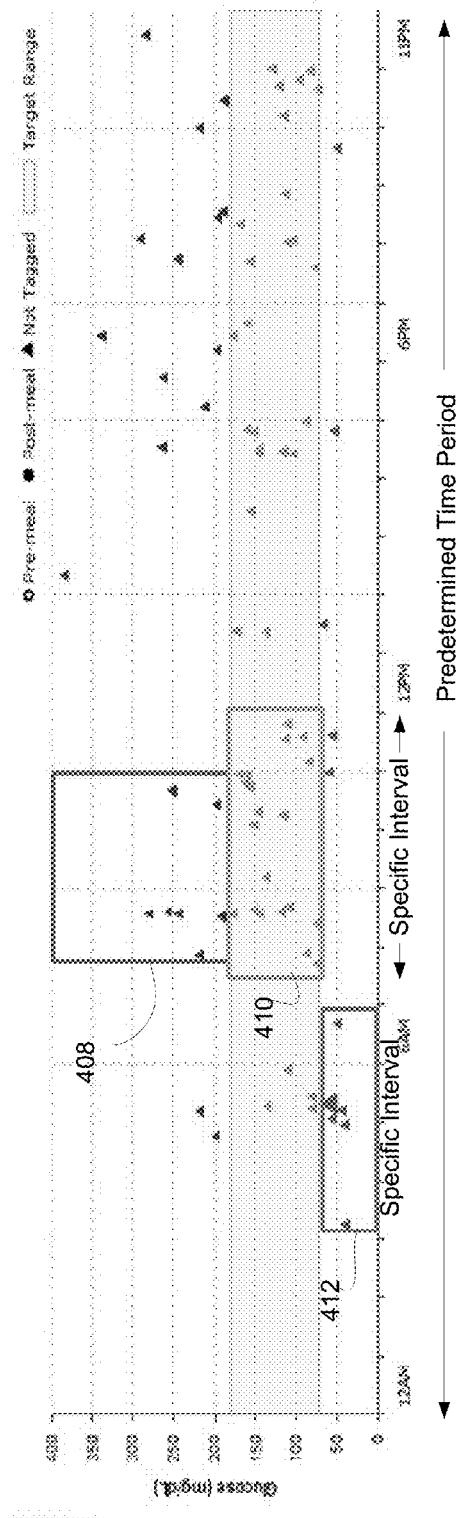
Fig. 4A
Fig. 4B

METHOD AND SYSTEM TO DERIVE GLYCEMIC PATTERNS FROM CLUSTERING OF GLUCOSE DATA

BACKGROUND

Diabetes mellitus is a chronic metabolic disorder caused by an inability of the pancreas to produce sufficient amounts of the hormone drug so that the metabolism is unable to provide for the proper absorption of sugar and starch. This failure leads to hyperglycemia, i.e. the presence of an excessive amount of analyte within the blood plasma. Persistent hyperglycemia has been associated with a variety of serious symptoms and life threatening long term complications such as dehydration, ketoacidosis, diabetic coma, cardiovascular diseases, chronic renal failure, retinal damage and nerve damages with the risk of amputation of extremities. Because healing is not yet possible, a permanent therapy is necessary which provides constant glycemic control in order to always maintain the level of blood analyte within normal limits. Such glycemic control is achieved by regularly supplying external drug to the body of the patient to thereby reduce the elevated levels of blood analyte.

An external drug was commonly administered by means of multiple, daily injections of a mixture of rapid and intermediate acting drugs via a hypodermic syringe. While this treatment does not require the frequent estimation of blood analyte, it has been found that the degree of glycemic control achievable in this way is suboptimal because the delivery is unlike physiological drug production, according to which drug enters the bloodstream at a lower rate and over a more extended period of time. Improved glycemic control may be achieved by the so-called intensive drug therapy which is based on multiple daily injections, including one or two injections per day of long acting drug for providing basal drug and additional injections of rapidly acting drug before each meal in an amount proportional to the size of the meal. Although traditional syringes have at least partly been replaced by drug pens, the frequent injections are nevertheless very inconvenient for the patient, particularly those who are incapable of reliably self-administering injections.

Substantial improvements in diabetes therapy have been achieved by the development of the drug delivery device, relieving the patient of the need for syringes or drug pens and the administration of multiple, daily injections. The drug delivery device allows for the delivery of drug in a manner that bears greater similarity to the naturally occurring physiological processes and can be controlled to follow standard or individually modified protocols to give the patient better glycemic control.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body and are generally controlled via a user interface built-in to the device or on a separate remote device.

Drug delivery devices have been utilized to assist in the management of diabetes by infusing drug or a suitable biologically effective material into the diabetic patient at a basal rate with additional drug or "bolus" to account for meals or high analyte values, levels or concentrations. The drug delivery device is connected to an infuser, better known as an infusion set by a flexible hose. The infuser typically has a subcutaneous cannula, adhesive backed mount on which the cannula is attached thereto. The cannula may include a quick disconnect to allow the cannula and mount to remain in place on the skin surface of the user while the flexible tubing is disconnected from the infuser. Regardless of the type of drug delivery device, blood analyte monitoring is required to achieve acceptable glycemic control. For example, delivery of suitable amounts of drug by the drug delivery device requires that the patient frequently determines his or her blood analyte level and manually input this value into a user interface for the external pump, which then calculates a suitable modification to the default or currently in-use drug delivery protocol, i.e. dosage and timing, and subsequently communicates with the drug delivery device to adjust its operation accordingly. The determination of blood analyte concentration is typically performed by means of an episodic measuring device such as a hand-held electronic meter which receives blood samples via enzyme-based test strips and calculates the blood analyte value based on the enzymatic reaction.

In recent years, continuous analyte monitoring has also been utilized with drug delivery devices to allow for greater control of the drug(s) being infused into the diabetic patients. In addition to glucose monitoring, people with diabetes often have to perform drug therapy such as, for example, insulin dosing. People with diabetes may self-administer insulin to reduce their blood glucose concentration. There are a number of mechanical devices currently available which enable an individual to dose a predetermined quantity of insulin such as, for example, a hypodermic syringe, an insulin pen, and an insulin pump. One such insulin pump is the Animas® Ping, a product which is manufactured by Animas Corporation. Another is the Animas® Vibe, also manufactured by Animas Corporation.

People with diabetes should maintain tight control over their lifestyle, so that they are not adversely affected by, for example, irregular food consumption or exercise. In addition, a physician dealing with a particular individual with diabetes may require detailed information on the individual's lifestyle to provide effective treatment or modification of treatment for controlling diabetes. Currently, one of the ways of monitoring the lifestyle of an individual with diabetes has been for the individual to keep a paper logbook of their lifestyle. Another way is for an individual to simply rely on remembering facts about their lifestyle and then relay these details to their physician on each visit.

The aforementioned methods of recording lifestyle information are inherently difficult, time consuming, and possibly inaccurate. Paper logbooks are not necessarily always carried by an individual and may not be accurately completed when required. Such paper logbooks are small and it is therefore difficult to enter detailed information requiring detailed descriptors of lifestyle events. Furthermore, an individual may often forget key facts about their lifestyle when questioned by a physician who has to manually review and interpret information from a hand-written notebook. There is no analysis provided by the paper logbook to distill or separate the component information. Also, there are no graphical reductions or summary of the information. Entry of data into a secondary data storage system, such as a database or other electronic systems, requires a laborious transcription of information, including lifestyle data, into this secondary data storage. Difficulty of data recordation encourages retrospective entry of pertinent information that results in inaccurate and incomplete records.

SUMMARY OF THE DISCLOSURE

Applicant has discovered techniques for determining clusters of data that can be utilized to provide significant insights to the person with diabetes. In one embodiment, a system for management of diabetes of a subject is provided that includes at least one glucose monitor and a controller operatively connected to the at least one glucose monitor. The at least one glucose monitor is configured to measure a glucose concentration based on an enzymatic reaction with physiological fluid in a biosensor that provides an electrical signal representative of the glucose concentration. The controller is in communication with at least one glucose monitor and configured to receive or transmit glucose data representative of glucose levels measured by the glucose monitor over a predetermined time period to determine plural clusters of glucose data with respect to glucose levels and the predetermined time so that the glucose levels with reference to a predetermined time period are correlated to each other in a cluster due to their similarity as compared to glucose levels in other clusters. And in this system, the controller annunciates a message whenever at least a cluster in which a number (N) of glucose measurements of each cluster is divided into a total number of days (D) on which the glucose measurements were taken in a specific time interval of a day (SID) and the result (N/D) divided into the specific time interval in a day (SID) is less than a predetermined threshold so that the subject is notified that the number of glucose measurements is less than optimum for management of diabetes.

In yet another aspect, a system for management of diabetes of a subject. The system is provided that includes at least one glucose monitor and a controller. The at least one glucose monitor is configured to measure a glucose concentration based on an enzymatic reaction with physiological fluid in a biosensor that provides an electrical signal representative of the glucose concentration. The controller is in communication with at least one glucose monitor, and configured to receive or transmit glucose data representative of glucose levels measured by the glucose monitor over a predetermined time period to determine plural clusters of glucose data with respect to glucose levels so that the glucose levels with reference to a predetermined time period are correlated to each other in a cluster due to their similarity as compared to glucose levels in other clusters and at least three clusters of glucose levels are provided to indicate the distribution of the glucose levels. And in this system, the controller annunciates an indication of the distribution of the at least three clusters into respective first range, second range, and third range of glucose values.

In yet a further embodiment, a method for managing diabetes of a user with at least a glucose monitor and an infusion pump which are coupled to controller is provided. The method can be achieved by: conducting a plurality of glucose measurements over time with the at least one glucose monitor; collating the plurality of glucose measurements into clusters for a predetermined time period; in the event that the clusters indicate gaps in the glucose measurements during the predetermined time period, annunciating such gaps to the user; in the event that the clusters indicate that the clusters are converging towards a certain range of glucose values, annunciating that the clusters are trending towards such range; or in the event that the clusters indicate three different ranges of glucose values in which one cluster has a boundary greater than 180 mg/dL, annunciating to the user a glucose range that is intermediate in value between 180 mg/dL and the boundary.

In these foregoing embodiments, the following features may be used in various permutations with each other and the foregoing embodiment. For example, in the system, the annunciating of gaps comprises informing the user whenever at least a cluster in which a number (N) of glucose measurements of each cluster is divided into a total number of days (D) on which the glucose measurements were taken in a specific time interval of a day (SID) and the result (N/D) divided into the specific time interval in a day (SID) is less than a predetermined threshold; the specific time interval in a day comprises at least one of an overnight interval from about 10 PM to about 6 AM; a day interval from about 6 AM to about 5 PM; or a night interval from about 5 PM to about 10 PM; the predetermined threshold for the night interval comprises about 0.17 tests per hour-day; the predetermined threshold for the day interval comprises about 0.095 tests per hour-day; the message comprises a suggestion of which specific time interval to obtain more glucose measurements; the first range of glucose values comprises a minimum greater than a maximum of the second range, which has a minimum greater than a maximum of the first range; the minimum of the first range comprises about 180 mg/dL of glucose, the minimum of the second range comprises about 70 mg/dL; each of the clusters comprises glucose measurements with respect specific time intervals within the predetermined time period so that a message of a distribution of at least one cluster within one of the first, second and third ranges is annunciated.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIGS. 4A and 4B illustrate outputs of insights gleaned from trends or convergence of the glucose measurement data with clustering of the data.

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. Furthermore, the term "user" includes not only the patient using a drug infusion device but also the caretakers (e.g., parent or guardian, nursing staff or home care employee). The term "drug" may include pharmaceuticals or other chemicals that causes a biological response in the body of a user or patient.

Figure 1:
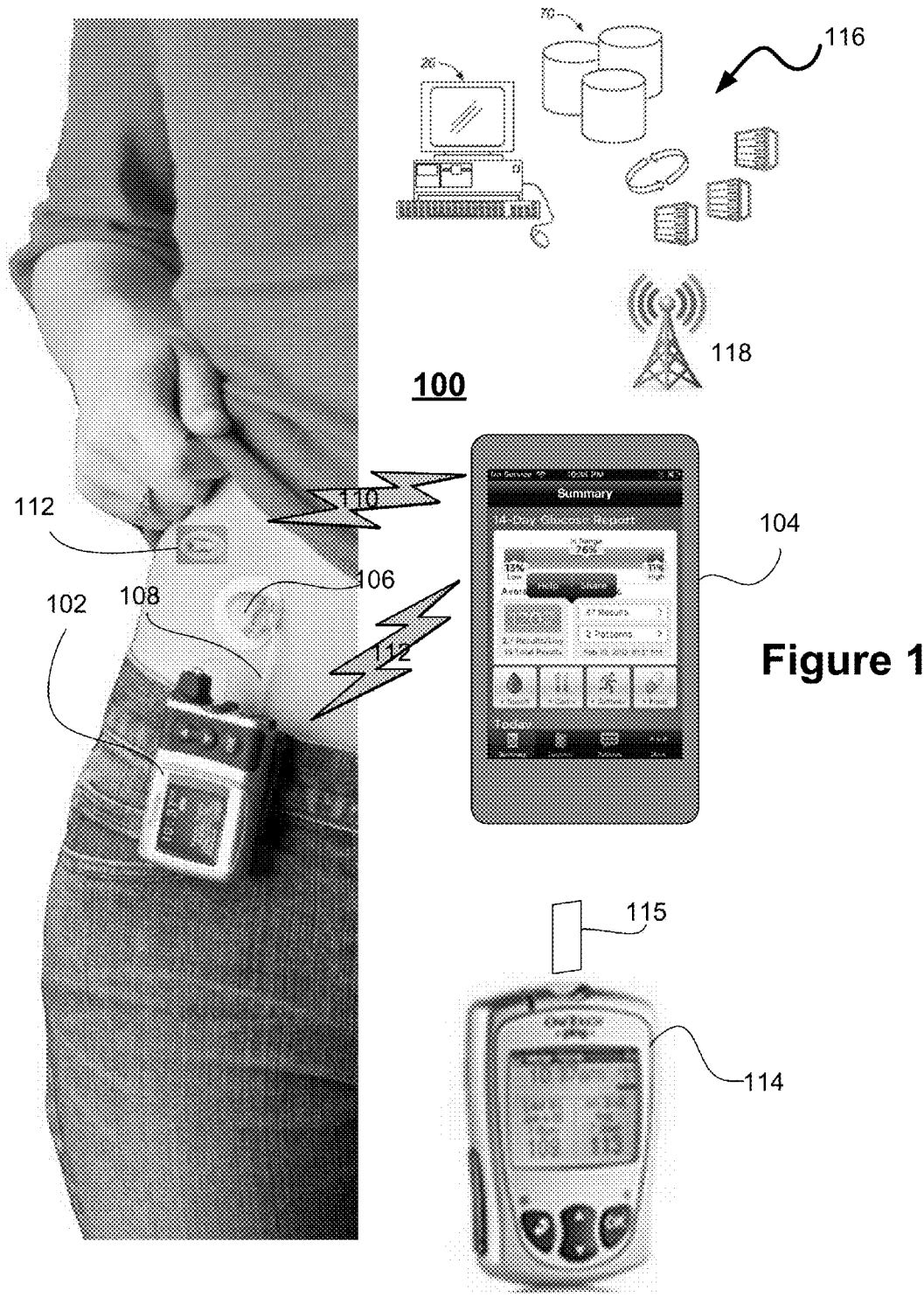
FIG. 1 illustrates an exemplary embodiment of the diabetic management system.

FIG. 1 illustrates a drug delivery system 100 according to an exemplary embodiment. Drug delivery system 100 includes a drug delivery device 102 and a remote controller 104. Drug delivery device 102 is connected to an infusion set 106 via flexible tubing 108.

Drug delivery device 102 is configured to transmit and receive data to and from remote controller 104 by, for example, radio frequency communication 110. Drug delivery device 102 may also function as a stand-alone device with its own built in micro controller or controller. In one embodiment, drug delivery device 102 is a drug infusion device and remote controller 104 is a hand-held portable controller. In such an embodiment, data transmitted from drug delivery device 102 to remote controller 104 may include information such as, for example, drug delivery data, blood glucose information, basal, bolus, insulin to carbohydrates ratio or insulin sensitivity factor, to name a few. The controller 104 may be configured to receive continuous analyte readings from a continuous analyte ("CGM") sensor 112. Data transmitted from remote controller 104 to drug delivery device 102 may include analyte test results and a food database to allow the drug delivery device 102 to calculate the amount of drug to be delivered by drug delivery device 102. Alternatively, the remote controller 104 may perform dosing or bolus calculation and send the results of such calculations to the drug delivery device 102. In an alternative embodiment, an episodic blood analyte meter 114 may be used alone or in conjunction with the CGM sensor 112 to provide data to either or both of the controller 104 and drug delivery device 102. Alternatively, the remote controller 104 may be combined with the meter 114 into either (a) an integrated monolithic device; or (b) two separable devices that are dockable with each other to form an integrated device. Each of the devices 102, 104, and 114 has a suitable micro-controller (not shown for brevity) programmed to carry out various functionalities. For example, a microcontroller can be in the form of a mixed signal microprocessor (MSP) for each of the devices 102, 104, or 114. Such MSP may be, for example, the Texas Instrument MSP 430, as described in patent application publication numbers US2010-0332445, and US2008-0312512 which are incorporated by reference in their entirety herein and attached hereto the Appendix of this application. The MSP 430 or the pre-existing microprocessor of each of these devices can be configured to also perform the method described and illustrated herein.

The measurement of glucose can be based on a physical transformation (i.e., the selective oxidation) of glucose by the enzyme glucose oxidase (GO). For example, in the strip type biosensor, the reactions that can occur in such biosensor are summarized below in Equations 1 and 2.

$$Glucose + GO_{(ox)} \rightarrow Gluconic\ Acid + GO_{(red)} \qquad \text{Eq. 1}$$

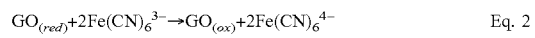
$$GO_{(red)} + 2Fe(CN)_6^{3-} \rightarrow GO_{(ox)} + 2Fe(CN)_6^{4-} \qquad \text{Eq. 2}$$

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the chemical reaction in Equation 1, the oxidized enzyme $GO_{(ox)}$ is transformed to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as illustrated in Equation 2. During the re-generation or transformation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test voltage applied between two electrodes, a test current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose can, therefore, be referred to as a glucose current.

Analyte levels or concentrations can also be determined by the use of the CGM sensor 112. The CGM sensor 112 utilizes amperometric electrochemical sensor technology to measure analyte with three electrodes operably connected to the sensor electronics and are covered by a sensing membrane and a biointerface membrane, which are attached by a clip. The top ends of the electrodes are in contact with an electrolyte phase (not shown), which may include a free-flowing fluid phase disposed between the sensing membrane and the electrodes. The sensing membrane may include an enzyme, e.g., analyte oxidase, which covers the electrolyte phase. In this exemplary sensor, the counter electrode is provided to balance the current generated by the species being measured at the working electrode. In the case of an analyte oxidase based glucose sensor, the species being measured at the working electrode is $H_2O_2$. The current that is produced at the working electrode (and flows through the circuitry to the counter electrode) is proportional to the diffusional flux of $H_2O_2$. Accordingly, a raw signal may be produced that is representative of the concentration of blood glucose in the user's body, and therefore may be utilized to estimate a meaningful blood glucose value. Details of the sensor and associated components are shown and described in U.S. Pat. No. 7,276,029, which is incorporated by reference herein as if fully set forth herein this application. In one embodiment, a continuous analyte sensor from the Dexcom Seven System (manufactured by Dexcom Inc.) can also be utilized with the exemplary embodiments described herein.

Drug delivery device 102 may also be configured for bi-directional wireless communication with a remote health monitoring station 116 through, for example, a wireless communication network 118. Remote controller 104 and remote monitoring station 116 may be configured for bi-directional wired communication through, for example, a telephone land based communication network. Remote monitoring station 116 may be used, for example, to download upgraded software to drug delivery device 102 and to process information from drug delivery device 102. Examples of remote monitoring station 116 may include, but are not limited to, a personal or networked computer, a personal digital assistant, other mobile telephone, a hospital base monitoring station or a dedicated remote clinical monitoring station.

Drug delivery device 102 includes processing electronics including a central processing unit and memory elements for storing control programs and operation data, a radio frequency module 116 for sending and receiving communication signals (i.e., messages) to/from remote controller 104, a display for providing operational information to the user, a plurality of navigational buttons for the user to input information, a battery for providing power to the system, an alarm (e.g., visual, auditory or tactile) for providing feedback to the user, a vibrator for providing feedback to the user, a drug delivery mechanism (e.g. a drug pump and drive mechanism) for forcing a drug from a drug reservoir (e.g., a drug cartridge) through a side port connected to an infusion set 106 and into the body of the user.

The components of the system described in relation to FIG. 1 are helpful to the person with diabetes in managing their disease. However, to achieve the efficacy in management of the disease, the person with diabetes would need more than just these components. As applicant has recognized, the component or the system must be able to provide easy to understand information that assist in the decision making of the person. To assist in this, applicant has devised a system that provides insights into the glucose measurements obtained for management of diabetes of a subject.

Figure 2:
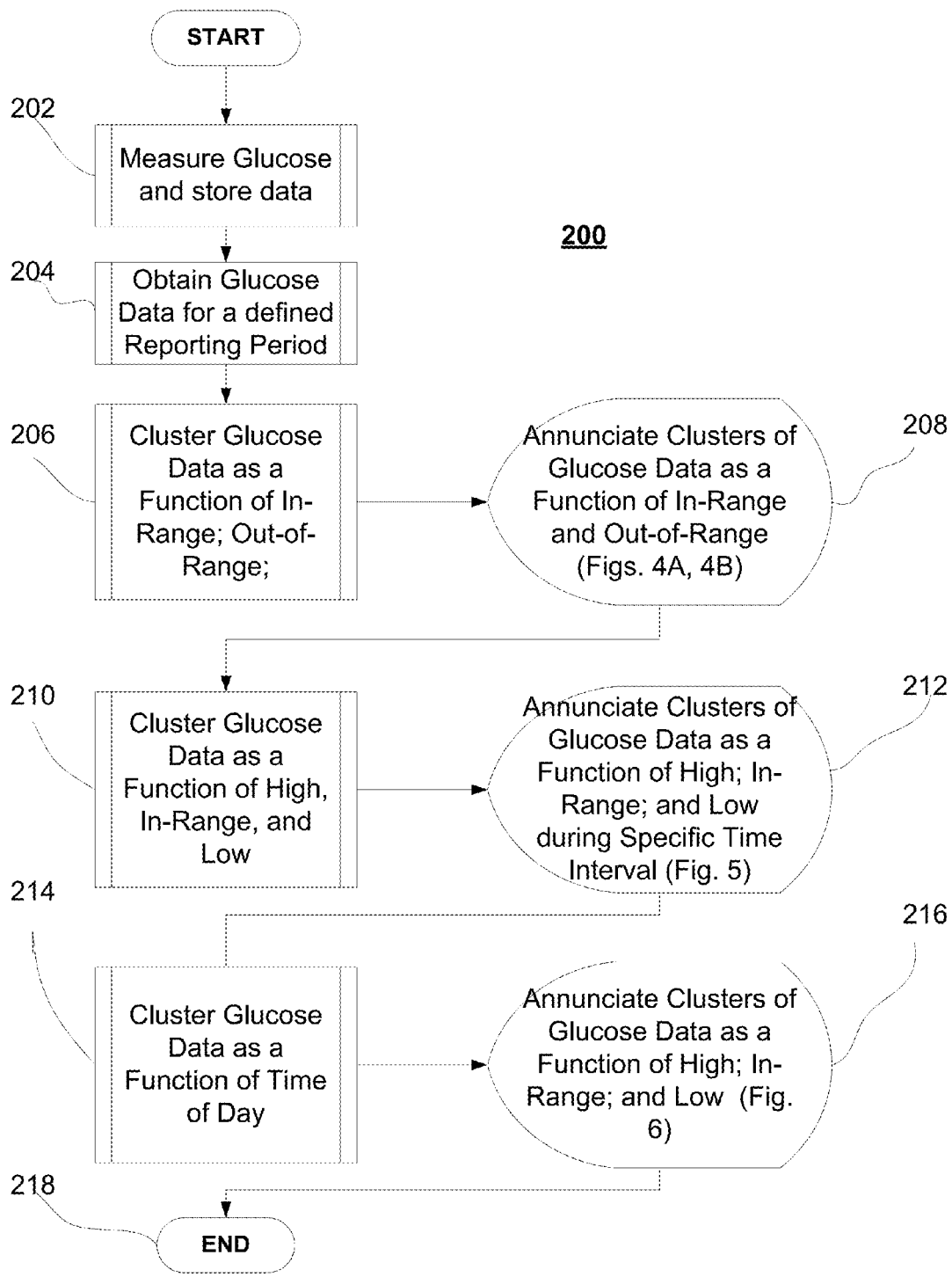
FIG. 2 illustrates an exemplary logic 200 of the technique utilized by the system of FIG. 1.

For the system of FIG. 1 to operate in accordance with applicant's new technique, a controller 104 is set up to be in communication with at least one glucose monitor (SMBG, CGM, or both). The controller 104 is configured to receive or transmit glucose data representative of glucose levels measured by the glucose monitor over a predetermined time period. By doing this, the controller 104, in accordance with the logic 200 of FIG. 2, is able to determine clusters of glucose data with respect to glucose levels and the predetermined time so that the glucose levels with reference to a predetermined time period are correlated to each other in a cluster due to their similarity as compared to glucose levels in other clusters.

In particular, the logic 200 begins with measurements of glucose data with the glucose monitor at step 202. The glucose data may include more than just the glucose concentration such as, for example, date, time, user's flags and other suitable records related to diabetes. For brevity, the discussion will use glucose data but it should be clear that the embodiments herein are not limited to solely glucose measurements.

At step 204, the data is obtained by the controller 104 for a defined reporting period, such as, for example, in the last 7 days, 21 days, 30 days or any number of days as set by the user. At step 206, the collated data from step 204 is "clustered" using a suitable cluster determination technique, such as, for example, the "K-mean clustering" technique.

"K means clustering" was developed by J. MacQueen (1967) and then by J. A. Hartigan and M. A. Wong around 1975. K-means clustering is a technique to classify or to group your data objects as a function of attributes into k group where k is a positive integer number. The technique involves finding and minimizing the sum of squares of distances between data objects and one or more centroids of the data objects. Additional details of the technique are shown and described in "Algorithm AS 136: A K-Means Clustering Algorithm" by J. A. Hartigan and M. A. Wong *Journal of the Royal Statistical Society. Series C (Applied Statistics)* Vol. 28, No. 1 (1979), pp. 100-108 Published by: Wiley-Blackwell at http://home.dei.polimi.it/matteucc/Clustering/tutorial_html/index.html. Other examples can be found in Chapter 8 of the book "Introduction to Data Mining" by Pang-Ning Tan, Michigan State University, Michael Steinbach, University of Minnesota and Vipin Kumar, University of Minnesota, Publisher: Addison-Wesley (2006).

Figure 3A:
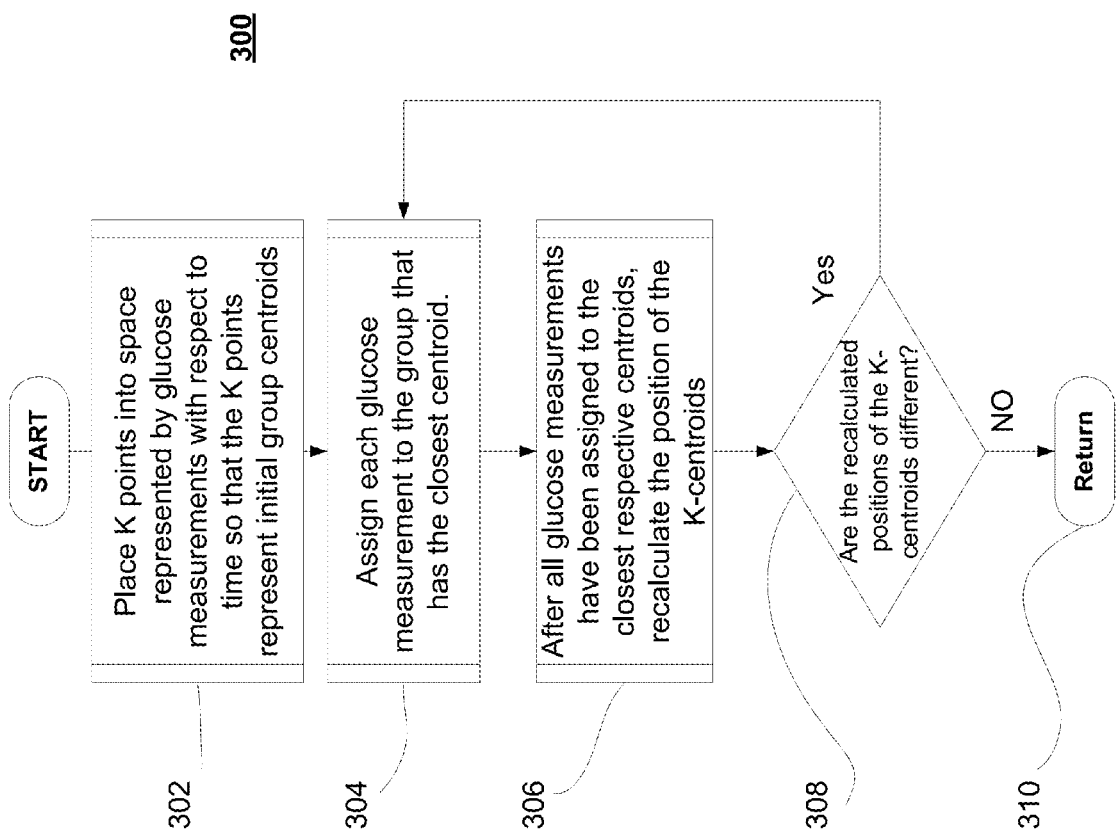
FIG. 3A illustrates the clustering technique 300 utilized by the logic of FIG. 2.
Figure 3B:
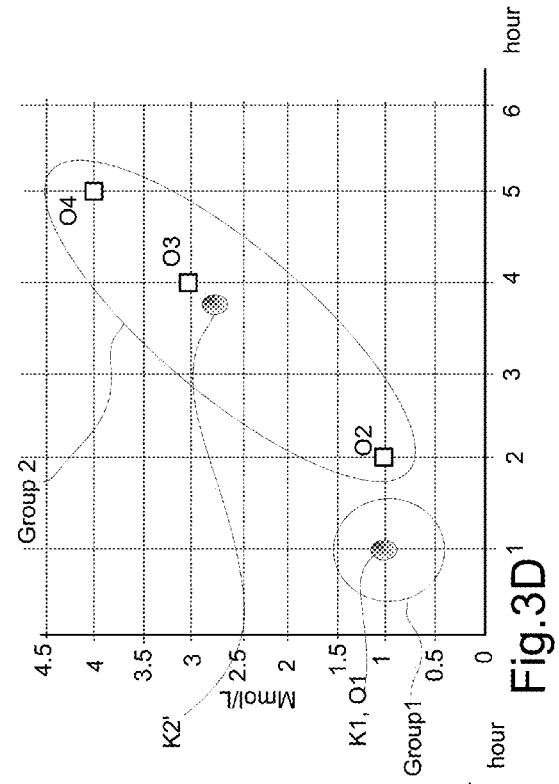
FIGS. 3B, 3C, 3D, and 3E illustrate a simplified example of the clustering technique of FIG. 3.
Figure 3D:
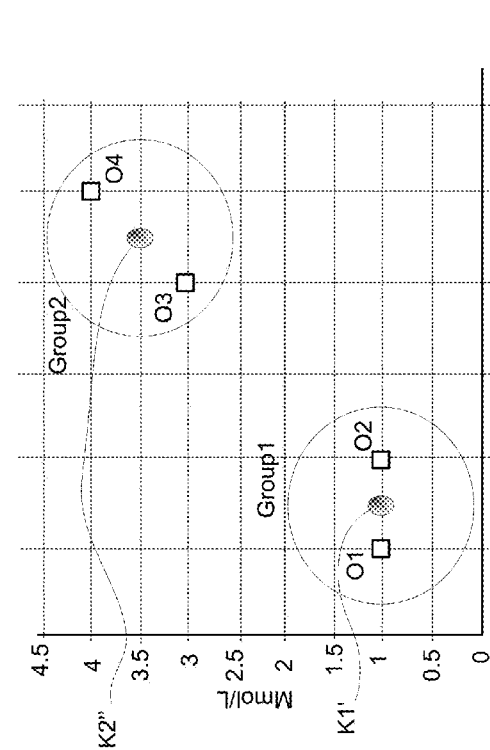
Figure 3C:
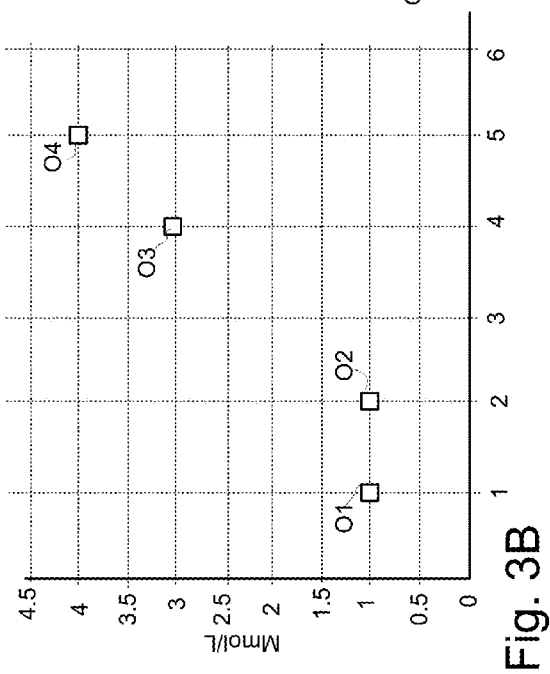

Specifically, the technique involves the following steps shown in process 300 of FIG. 3A. At step 302, arbitrary K points can be placed into space represented by the glucose measurements with respect to time so that these K points represent initial group centroids. This can be seen in the example of FIG. 3B where four data points O1, O2, O3, and O4 are utilized for brevity in this example. At step 304, each glucose measurements O1, O2, O3, and O4 to the group that has the closest centroid to the glucose measurement(s). For this example, two centroids K1 and K2 are arbitrarily selected in FIG. 3C. The distance from data point O3 to K1 and K2 are calculated along with the distance from O4 and K1 and K2 are calculated. As an example, the minimum distance from O4 to K1 is $d_{O4-k1} = \sqrt{(4-1)^2 + (3-1)^2}$ or 3.61 and the minimum distance from O4 to K2 $d_{O4-k2} = \sqrt{(4-2)^2 + (3-1)^2}$ or 2.83. At step 304, the glucose data O1, O2, O3, and O4 are assigned based on the minimum distance to the centroids K1 and K2. As can be seen in FIG. 3D, the glucose measurement O1 is within Group 1 in which K1 is also the centroid for Group 1. Measurements O2, O3, and O4 are part of group 2 closest to centroid K1. In step 306, after all glucose measurements have been assigned to the closest respective centroids, recalculate the position of the K-centroids and relocate the centroids if needed to ensure the minimum distance between the data points and the relevant centroid(s). In FIG. 3D, it is noted that Group 2 has three members (O2, O3, and O4), then the centroid of Group 2 (denoted by K2') is the average distance between the three members (3.7 hours by 2.7 mMol/dL). At step 306, the minimum distance from each data object to the centroids (including the new centroid K2') is calculated and the minimum distance is calculated from each object to the new centroid K2'. Due to the minimum distance from O2 to centroid K1, O2 belongs to Group 1.

Figure 3E:
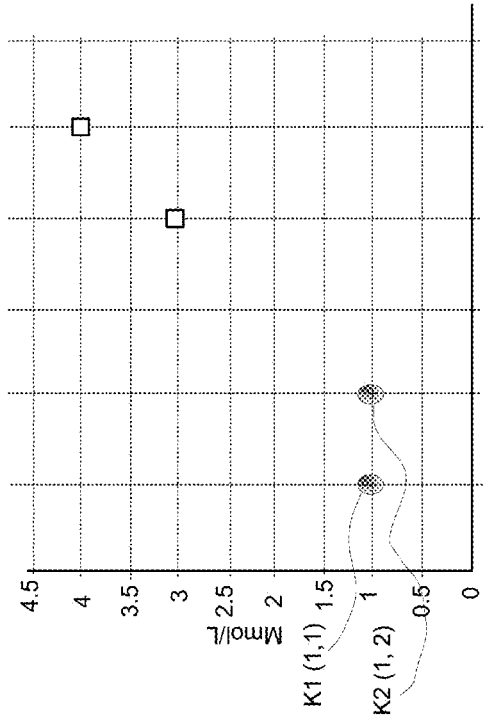

It can be seen that, in FIG. 4D, another iteration is needed to ensure the minimum distance from the data point(s) to the relevant centroid(s). As such, with reference to FIG. 3E, a new centroid K1' is calculated based on the average distance between members O1 and O2 and designated in FIG. 3E. A new centroid K2" is calculated based on the average distance between members O3 and O4 being in Group 2. Steps 304 and 306 are repeated until the centroids can no longer be relocated in order to meet the minimum distance rule. In the example in FIG. 3E, the centroid K1' and K2" do not move any longer as these centroids have reached a local optima while also satisfy the requirements of the clustering algorithm. This produces a separation of the objects into groups (e.g., Groups 1 and 2 of FIG. 3E) based on a rational basis for this clustering.

In actual data, shown here in FIG. 4A, data deemed to be "above range" of 170 mg/dL have been grouped in cluster 402 while data deemed to be within the range of 70 mg/dL to 170 mg/dL are grouped in cluster 404 and whereas data deemed to be below range of 70 mg/dL are grouped in cluster 406. This signifies to the user of the extent to which the glucose data are mostly in range and notably out of range in clusters 404 and 406 at substantially the same time interval from about 3 AM to about 9 AM. In contrast, the clustering of FIG. 4B shows that the above range cluster 408 generally coincides with the in-range cluster 410. Both clusters 410 and 412 do not coincide in the same time interval (3 AM-7 AM) for the below range cluster 412. As shown in FIG. 2, messages can be annunciated to the user of the disparities in the clusters based on the time intervals of the clusters. That is, each of the clusters (e.g. 402, 404, 406, 408, 410, 412) may include glucose measurements with respect specific time intervals within the predetermined time period so that an indication of a distribution of at least one cluster within one of the first, second and third ranges is annunciated, e.g., FIG. 4A or 4B. As used herein, the term "annunciated" and variations on the root term indicate that an announcement may be provided via text, audio, visual or a combination of all modes of communication to a user, a caretaker of the user or a healthcare provider.

Alternatively, a suggested testing frequency can be identified from a standard mapping taking into account the time of day and length of timeslot from, for example, Table 1.

TABLE I

| Time of Day | Tests/hour-Day |
|---|---|
| Overnight (10 PM-6 AM) | 0.125 Tests/hour-Day |
| Day (6 AM-5 PM) | 0.1 Tests/hour-Day |
| Night (5 PM-10 PM) | 0.1667 Tests/hour-Day |

For a timeslot closest to Night that spanned 4 hours, and had 10 tests over a 14 day period, the timeslot would average 0.71 tests/day, and over the 4 hours, the timeslot would average 0.179 tests/hour-day. This is above the limit of 0.1667 tests/hour-Day and would be considered sufficient.

For a timeslot closest to Day that spanned 6 hours, and had 8 tests over a 14 day period, the timeslot would average 0.57 tests/day, and over the 6 hours, the timeslot would average 0.095 tests/hour-day. This is above the limit of 0.095 tests/hour-Day and would be considered insufficient.

The message would indicate the timeslot, and how many more readings each week that should be added to reach adequacy. For example, the system may output "you have inadequate testing from 12 PM-6 PM. You should test 0.5 times more each week in this timeslot to reach adequacy."

Figure 5:
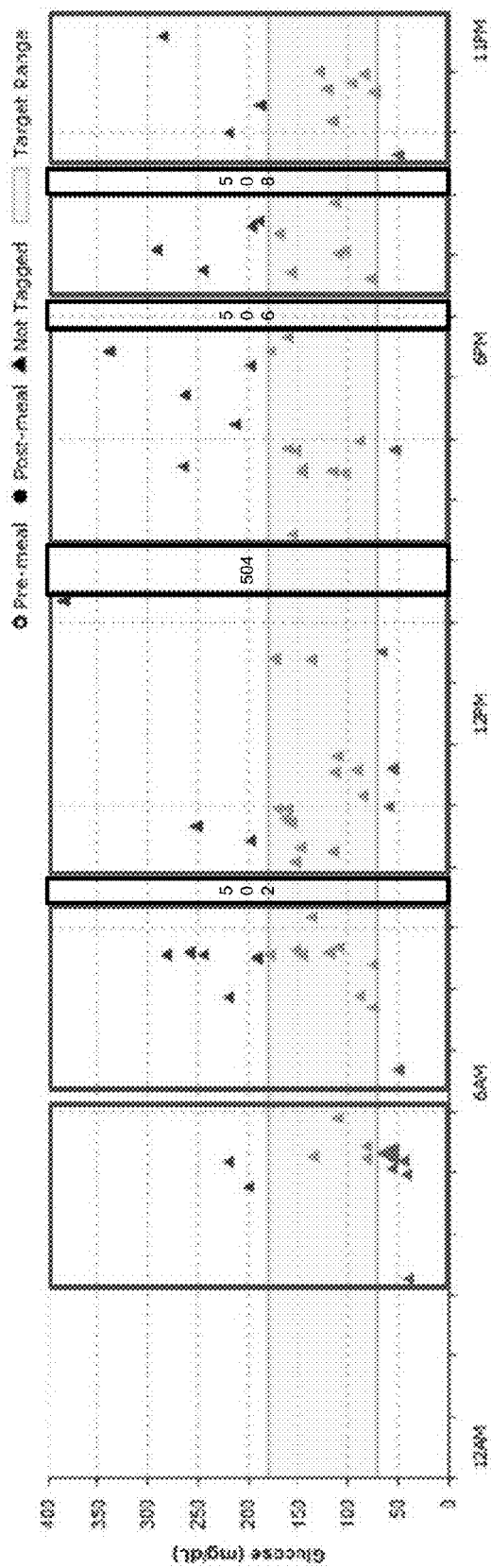
FIG. 5 illustrates an output to show gaps in the glucose measurements with the use of clustering of glucose data.

The visualization would highlight the timeslot that required more testing indicating target tests/week for each timeslot and actual tests per week in each timeslot, such as, for example, visually in FIG. 5 or textually in Table II.

As shown in FIG. 5, areas 502, 504, 506, and 508 can be used by the system to indicate that there are gaps in when the user has conducted glucose measurements. Where the user is using a CGM, this visualization can be used by the user or HCP to determine whether there are problems with the CGM data due to gaps in the output data.

In Table II below, a textual indication can be provided to the user that actual glucose measurements at 4.2 measurements per week do not meet the recommended tests per week (e.g., 5.25) during a specific time interval from 12 AM to 6 AM and that the actual measurements at 4.2 tests per week do not meet the recommended measurements per week during the specific time interval from 12 PM to 6 PM during a predetermined range of time (e.g., one-week).

TABLE II

| | 12 AM-6 AM | 6 AM-8 AM | 8 AM-10 AM | 10 AM-12 PM | 12 PM-6 PM | 6 PM-9 PM | 9 PM-12 AM |
|---|---|---|---|---|---|---|---|
| Tests/Wk | 4.2 | 2 | 1.5 | 1.5 | 4 | 3.75 | 3 |
| Recommended Tests/Wk | 5.25 | 1.4 | 1.4 | 1.47 | 4.2 | 3.5 | 2.625 |

To recap, the controller 104 may annunciate a message whenever at least a cluster in which a number (N) of glucose measurements of each cluster is divided into a total number of days (D) on which the glucose measurements were taken in a specific time interval of a day (SID) and the result (N/D) divided into the specific time interval in a day (SID) is less than a predetermined threshold so that the subject is notified that the number of glucose measurements is less than optimum for management of diabetes. In this message, the specific time interval in a day may include at least one of an overnight interval from about 10 PM to about 6 AM; a day interval from about 6 AM to about 5 PM; or a night interval from about 5 PM to about 10 PM; the predetermined threshold for the night interval may include about 0.17 tests per hour-day; the predetermined threshold for the day interval may include about 0.095 tests per hour-day.

When analyzing blood glucose data, a target range is often used to categorize a specific SMBG reading as being good or bad for a patient. There are established recommended ranges for patients, but in many cases doctors may customize the range. For patients, however, bringing their glucose under control and into the suggested range can seem daunting, especially when a patient is initially out of control with respect to glucose.

Figure 6:
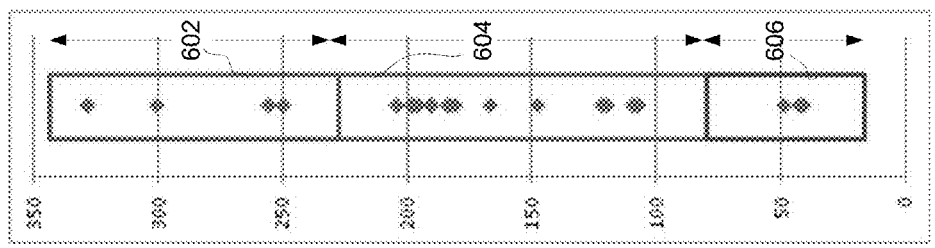
FIG. 6 illustrates an output of where the patient's glucose data fall into three different clusters as compared to the expected range of glucose measurements for a person with diabetes.

With reference to FIG. 6, the controller 104 can determine clusters of glucose data with respect to glucose levels such that at least three clusters of glucose levels are provided to indicate the distribution of the glucose levels. As shown in FIG. 6, the technique will always identify 3 clusters of data but these clusters are not fixed to specific ranges but rather are defined by the three clusters themselves. For example, the measurements are collated into the following 3 clusters: High Cluster 602 (ranging from about 225-335 mg/dL); a Mid-Range cluster 604 (ranging from about 80 mg/dL-225 mg/dL); and a Low Cluster 606 (ranging from about 45 mg/dL-50 mg/dL). Due to the clustering of the data, the users' mid-range cluster 604 falls at about 80 mg/dL to about 225 mg/dL. It is noted that an ideal range would have all users managing to a range of about 70 mg/dL-130 mg/dL.

For picking a high range, the logic could compare user's current high end of the mid-range cluster to the ideal. In this case, the glucose concentration of 225 mg/dL would be compared to the ideal 130 mg/dL. It would be desirable to the subject to manage the glucose concentration to a range under 130 mg/dL, but in fact the user currently has enough high readings to form a cluster with a boundary at 225. Changing a subject's glucose concentration from 225 mg/dL down to 130 mg/dL may seem like a daunting task, and the system may suggest a 10% improvement over the current clustering, and recommend a high range of 202 mg/dL for now. This smaller goal improvement may be more manageable for the user, and the analysis would be re-run, and should be more tightly controlled data in the future after the user has better managed to the new recommended range.

For picking a low range, the logic could compare the user's current low-end of the mid-range cluster to the ideal. In this case, 80 would be compared to 70. For the system to maintain adequate safeguard against triggering an indication of hypoglycemia, it might not be desirable to make the low higher than the ideal low of 70. As such, the system would recommend 70 mg/dL as the low range (i.e., simply recommending the ideal target).

Other variations are possible for this embodiment. For example, the system's logic can be run separately on pre-meal and post-meal data to provide recommended ranges for these categorizations of glucose readings. The logic can be run on older data sets to show progress over time. The logic may use the linear distance in SMBG or CGM readings for analysis, or it can use adjusted values intended to scale SMBG or CGM readings more appropriately.

Applicant notes that other clustering techniques can also be utilized in addition to or alternatively to the K-means clustering technique described herein. For example, the K-median clustering, Gaussian mixture model, or c-means fuzzy clustering can also be utilized. As such, embodiments of the present invention are not limited strictly to the clustering technique described herein.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method for managing diabetes of a user with at least a glucose monitor and an infusion pump which are coupled to a controller, the method comprising the steps of:
    conducting a plurality of glucose measurements over time with the at least one glucose monitor;
    collating, using the controller, the plurality of glucose measurements into clusters for a predetermined time period;
    in the event that the clusters indicate gaps in the glucose measurements during the predetermined time period, annunciating, using the controller, such gaps to the user;
    in the event that the clusters indicate that the clusters are converging towards a certain range of glucose values, annunciating, using the controller, that the clusters are trending towards such range; or
    in the event that the clusters indicate three different ranges of glucose values for the predetermined time period including a high range, a mid-range, and a low range, comparing, using the controller, an upper boundary of the mid-range to an upper boundary of a predetermined ideal range, comparing, using the controller, a lower boundary of the mid-range to a lower boundary of the predetermined ideal range, and annunciating, using the controller, to the user whether the mid-range is outside the predetermined ideal range of a glucose range that is intermediate in value between 180 mg/dL and the boundary.

2. The method of claim 1, in which the annunciating of gaps comprises informing the user whenever at least a cluster in which a number (N) of glucose measurements of each cluster is divided into a total number of days (D) on which the glucose measurements were taken in a specific time interval of a day (SID) and the result (N/D) divided into the specific time interval in a day (SID) is less than a predetermined threshold.

3. The method of claim 2, in which the specific time interval in a day comprises at least one of an overnight interval from about 10 PM to about 6 AM; a day interval from about 6 AM to about 5 PM; or a night interval from about 5 PM to about 10 PM.

4. The method of claim 3, in which the predetermined threshold for the night interval comprises about 0.17 tests per hour-day.

5. The method of claim 3, in which the predetermined threshold for the day interval comprises about 0.095 tests per hour-day.

6. The method of claim 3, in which the message comprises a suggestion of which specific time interval to obtain more glucose measurements.

7. A system for management of diabetes of a subject, the system comprising:
    at least one glucose monitor that is configured to measure a glucose concentration based on an enzymatic reaction with physiological fluid in a biosensor that provides an electrical signal representative of the glucose concentration; and
    a controller in communication with at least one glucose monitor, the controller being configured to receive or transmit glucose data representative of glucose levels measured by the glucose monitor over a predetermined time period to determine plural clusters of glucose data with respect to glucose levels and the predetermined time so that the glucose levels with reference to a predetermined time period are correlated to each other in a cluster due to their similarity as compared to glucose levels in other clusters; and
    wherein the controller annunciates a message whenever at least a cluster in which a number (N) of glucose measurements of each cluster is divided into a total number of days (D) on which the glucose measurements were taken in a specific time interval of a day (SID) and the result (N/D) divided into the specific time interval in a day (SID) is less than a predetermined threshold so that the subject is notified that the number of glucose measurements taken within the specific time interval of the day (SID) over the total number of days is less than optimum for management of diabetes.

8. The system of claim 7, in which the specific time interval in a day comprises at least one of an overnight interval from about 10 PM to about 6 AM; a day interval from about 6 AM to about 5 PM; or a night interval from about 5 PM to about 10 PM.

9. The system of claim 8, in which the predetermined threshold for the night interval comprises about 0.17 tests per hour-day.

10. The system of claim 8, in which the predetermined threshold for the day interval comprises about 0.095 tests per hour-day.

11. The system of claim 8, in which the message comprises a suggestion of which specific time interval to obtain more glucose measurements.

* * * * *